US005595911A

United States Patent [19]
Tonks

[11] Patent Number: 5,595,911
[45] Date of Patent: Jan. 21, 1997

[54] ISOLATION OF A CDNA ENCODING A PROTEIN TYROSINE PHOSPHATASE WHICH LOCALIZES TO FOCAL ADHESIONS

[75] Inventor: Nicholas K. Tonks, Cold Spring Harbor, N.Y.

[73] Assignee: Cold Spring Harbor Laboratory, Cold Spring Harbor, N.Y.

[21] Appl. No.: 107,420

[22] Filed: Aug. 16, 1993

Related U.S. Application Data

[63] Continuation of Ser. No. 663,579, Mar. 1, 1991, abandoned, which is a continuation-in-part of Ser. No. 494,036, Mar. 14, 1990, abandoned.

[51] Int. Cl.[6] ............................. C12N 15/54; C12N 9/12
[52] U.S. Cl. ....................... 435/320.1; 435/194; 536/23.2
[58] Field of Search .......................... 536/23.2; 435/194, 435/320.1

[56] References Cited

PUBLICATIONS

Rees, D. J. G. et al., *Nature*, 347:685–689 (1990).
Tonks, N. K. et al., *Biochemistry*, 27:8695–8701 (1988).
Streuli, M. et al., *The EMBO Journal*, 9:2399–2407 (1990).
Cool et al., *PNAS* vol. 86, pp. 5257–5261, Jul. 1989.

Charbonneau et al. *PNAS*, vol. 86, pp. 5252–5256, Jul. 1989.

Charbonneau et al., *PNAS*, vol. 85, pp. 7182–7186, Oct. 1988.

Suggs et al., *PNAS*, vol. 78, No. 11, pp. 6613–6617, Nov. 1981.

Reeck, et al., *Cell*, vol. 50, 667 Aug. 28, 1987.

*Primary Examiner*—Keith D. Hendricks
*Attorney, Agent, or Firm*—Hamilton, Brook, Smith & Reynolds, P.C.

[57] ABSTRACT

DNA which encodes a protein homologous to the protein tyrosine phosphatases (PTPases) which catalyze the dephosphorylation of proteins in which tyrosyl residues have been phosphorylated through the action of a protein kinase. The protein, which appears as if it will localize to focal adhesions, is also the subject of the present invention. In particular, it relates to cDNA encoding a protein, referred to as PTPH1.

7 Claims, 6 Drawing Sheets

```
        CTGCAGGTTATTCAGCGATAGTTATGACCTCCCGGTTACGTGCGTTGGGTGGAAGAATTAATAATATACGCACCTCGGAGTTACCCAAAGAGAAAACTCGATCAAGTC ATTGCAGC
                          M  T  S  R  L  R  A  L  G  G  R  I  N  N  I  R  T  S  E  L  P  K  E  K  T  R  S  E  V  I  C  S
  120   ATCCACTTTTTAGATGGCGTGGTACAGACCTTTAAAGTTACTAAACAAGACACTGGCCAGGTTCTTCTGGATATGGTGCACAACCACCTGGGTGTGACTGAAAAGGAATATTTTGGTTA
        I  H  F  L  D  G  V  V  Q  T  F  K  V  T  K  Q  D  T  G  Q  V  L  L  D  M  V  H  N  H  L  G  V  T  E  K  E  Y  F  G  L
  240   CAGCATGATGACGACTCCGTGGACTCTCCTAGATGGCTGGAAGCAAGCAAACCCATCAGGAAGCAGTTAAAAGGAGGTTTCCCCTGTACCCTGCATTTTGAGTAAGATTTTTATACCT
        Q  H  D  D  D  S  V  D  S  P  R  W  L  E  A  S  K  P  I  R  K  Q  L  K  G  F  P  C  T  L  H  F  R  V  R  F  I  P
  360   GATCCCAACACACTGCAGCAAGAACAAACCAGGCACTTGTATTTCTTACAACTGAAGATGGATATTTGCGAAGGAAGGTTAACCTGCCCTCTTAACTCAGCAGTTGGTTCTAGCGTCCTAT
        D  P  N  T  L  Q  Q  E  Q  T  R  H  L  Y  F  L  Q  L  K  M  D  I  C  E  G  R  L  T  C  P  L  N  S  A  V  V  L  A  S  Y
  480   GCCGTACAATCTCATTTTGGAGACTATAATTCTTCCATACATCATCCAGGCTATCTTTCCGATAGTCAGTTTATACCCGATCAAAATGAGGACTTTTTAACAAAAGTCGAATCTCTGCAT
        A  V  Q  S  H  F  G  D  Y  N  S  S  I  H  H  P  G  Y  L  S  D  S  H  F  I  P  D  Q  N  E  D  F  L  T  K  V  E  S  L  H
  600   GAGCAGCACAGTGGGCTAAAACAATCAGAAGCAGAATCCTGCTATATCAACATAGCCGGACCCTCGACTTCTATGGAGTAGAACTGCACAGTGGTAGGGATCTGCACAATTTAGACCTA
        E  Q  H  S  G  L  K  Q  S  E  A  E  S  C  Y  I  N  I  A  R  T  L  D  F  Y  G  V  E  L  H  S  G  R  D  L  H  N  L  D  L
  720   ATGATTGGAATTGCTTCCGCGGGTGTTGCTGTGTACCGAAAATACATTTGCACAAGTTTCTATCCTTGGGTGAACATTCTCAAAATTTCTTTCAAAAGGAAAAAGTTCTTCATACATCAG
        M  I  G  I  A  S  A  G  V  A  V  Y  R  K  Y  I  C  T  S  F  Y  P  W  V  N  I  L  K  I  S  F  K  R  K  K  F  F  I  H  Q
  840   CGACAGAAACAGGCTGAATCCAGGGAACATATTGTGGCCTTCAACATGCTGAATTACCGATCTTGCAAAAACTTGTGGAAATCCTGTGTTGAGCACCATACGTTCTTTCAGGCAAAGAAG
        R  Q  K  Q  A  E  S  R  E  H  I  V  A  F  N  M  L  N  Y  R  S  C  K  N  L  W  K  S  C  V  E  H  H  T  F  F  Q  A  K  K
  960   CTACTACCTCAGGAAAAGAATGTTCTGTCTCAGTACTGGACTATGGGCTCTCGGAACACCAAAAAGTCGGTAAATAACCAATATTGCAAAAAGGTGATTGGCGGGATGGTGTGGAACCCA
        L  L  P  Q  E  K  N  V  L  S  Q  Y  W  T  M  G  S  R  N  T  K  K  S  V  N  N  Q  Y  C  K  K  V  I  G  G  M  V  W  N  P
 1080   GCCATGCGGAGATCCTATCAGTGGAGCACTTAGAAACCAAGAGTCTGCCTTCTCGTTCCCTCCCATTACTCCCAACTGGCGAAGTCCTCGGCTCCGGCACGAAATCCGAAAGCCACGC
        A  M  R  R  S  L  S  V  E  H  L  E  T  K  S  L  P  S  R(S) P  P  I  T  P  N  W  R(S) P  R  L  R  H  E  I  R  K  P  R
 1200   CACTCTTCTGCAGATAACCTTGCAAATGAAATGACCTACATCACGGAAACGGAAGATGTATTTTACACGTACAAGGGCTCTCTGGCCCCTCAAGACAGCGATTCTGAAGTTTCTCAGAAC
        H  S  S  A  D  N  L  A  N  E  M  T  Y  I  T  E  T  E  D  V  F  Y  T  Y  K  G  S  L  A  P  Q  D  S  D  S  E  V  S  Q  N
 1320   CGAAGCCCGCCACCAAGAGAGTTTATCCGAGAACAATCCGGCACAAAGCTACCTGACCCAGAAGTCATCCAGTTCTGTGTCTCCATCTTCAAATGCTCCAGGCTCCTGCTCACCTGACGGC
        R (S) P  H  Q  E  S  L  S  E  N  N  P  A  Q  S  Y  L  T  Q  K  S  S  S  S  V  S  P  S  S  N  A  P  G  S  C  S  P  D  G
 1440   GTTGATCAGCAGCTCTTAGATGACTTCCACAGGGTGACCAAAGGGGGCTCCACCGAGGACGCCAGCCAGTACTACTGTGACAAGAATGATAATGGTGACAGCTACTTAGTCTTGATCCGT
        V  D  Q  Q  L  L  D  D  F  H  R  V  T  K  G  S  T  E  D  A  S  Q  Y  Y  C  D  K  N  D  N  G  D  S  Y  L  V  L  I  R
 1560   ATCACACCAGATGAAGATGAAAATTTGGATTTAATCTTAAGGGAGGAGTGGATCAAAAGATGCCTCTTGTGTATCAAGGATAAACCCAGAGTCACCTGCGGACACCTGCATTCCTAAG
        I  T  P  D  E  D  G  K  F  G  F  N  L  K  G  G  V  D  Q  K  M  P  L  V  V  S  R  I  N  P  E  S  P  A  D  T  C  I  P  K
 1680   CTGAACGAAGGGGATCAAATCGTGTTAATCAATGCCGGGACAATCTCAGAACACACGCATGACCAAGTGGTGATGTTCATCAAAGCCAGCCGGGAGTCCCACTCACGGGAGCTGGCCCTG
        L  N  E  G  D  Q  I  V  L  I  N  G  R  D  I  S  E  H  T  H  D  Q  V  V  M  F  I  K  A  S  R  E  S  H  S  R  E  L  A  L
```

| | |
|---|---|
| PTPH1 | ICSIHFLDGVVQTFKVTKQDTGQVLLDMVHNHLGVTEKEYFGLQHDDDSVDSPRWLEA |
| Human 4.1 | HCKVSLLDDTVYECVVEKHAKGQDLLKRVCEHLNLLEEDYFGLAIWDNA-TSKTWLDS |
| Human ezrin | INVRVTTMDAELEFAIQPNTTGKQLFDQVVKTIGLREVWYFGLHYVDNK-GFPTWLKL |
| Mouse talin | GITNHDEYSLVRELMEEKKDEGTGTLRKDKTLL-RDEKKMEKLKQKLHTDDELNWLDH |
| | |
| PTPH1 | SKPIRKQLKGGF--PCTLHFRVRFFIPDPNTLQQEQTRH-LYFLQLKMDICEGRLTCPL |
| Human 4.1 | AKEIKKQVRGV--PWNFTFNVKFYPPDPAQLTEDITRYYL-CLQLRQDIVAGRLPCSF |
| Human ezrin | DKKVSAQEVRKENPLQFKFRAKFYPEDVAEELIQDITQKLFFLQVKEGILSDEIYCPP |
| Mouse talin | GRTLREQGVEE--HETLLLRRKFFYSDQNVDSRDPVQLNLLYVQARDDILNGSHPVSF |
| | |
| PTPH1 | NSAVVLASYAVQSHFGDYNSSIHHPGYLSDSHFIPDQ------NEDFLTKVESLHE |
| Human 4.1 | ATLALLGSYTIQSELGDYDPELHGVDYVSDFKKLAPNQ------TKELEEKVMELHK |
| Human ezrin | ETAVLLGSYAVQAKFGDYNKEVHKSGYLSSERLIPQRVMDQHKLTRDQWEDRIQVWHA |
| Mouse talin | DKACEFAGFQCQIQFGPHNEQKHKAGFLDLKDFLPKE------YVKQKGERKIFQAHK |
| | |
| PTPH1 | QHSGLKQSEAESCYINIARTLDFYGVELHSGRDLHNLDLMIGIASAGVAVYRK------ |
| Human 4.1 | SYRSMTPAQADLEFLENAKKLSMYGVDLHKAKDLEGVDIILGVCSSGLLVYKD---- |
| Human ezrin | EHRGMLKDNAMLEYLKIAQDLEMYGINYFEIKNKKGTDLWLGVDALGLNIYEK---DDK |
| Mouse talin | NCGQMSEIEAKVRYVKLARSLKTYGVSFFLVKEKMKGKNKLVPRLLGITKECVMRVDE |
| | |
| PTPH1 | YICTSFYPWVNI--LKISFKRKKFFIHQRQKQAESREHIVAFNMLNYRSCKNLWKSCV |
| Human 4.1 | KLRINRFPWPKV--LKISYKRSSFFIKIRPGEQEQYESTIGFKLPSYRAAKKLWKVCV |
| Human ezrin | LTPKIGFPWSEI--RNISFNDKKFVIKPIDKKAPDFV----FYAPRLRINKRILQLCM |
| Mouse talin | KTKEVIQEWSLTNIKRWAASPKSFTLDFGDYQDGYYSVQTTEGEQIAQLIAGYIDIIL |
| | |
| PTPH1 | EHHTFFQAKKLLPQEKNVLSQYWTMGSRNTKKSVNNQYCKKVIGMVWNPAMRRS |
| Human 4.1 | EHHTTF---RLTSTDTIPKSKFLALGSK-FRYSGRTQAQTRQASALIDRPAPHFE |
| Human ezrin | GNHELYMRRKPDTIEVQQMKAQAREEKHQKQLERQQLETEKKRRETVEREKEQM |
| Mouse talin | KKKKSKDHFGLEGDEESTMLEDSVSPKKSTVLQQQYNRVGKVEHGSVALPAIMRS |

FIGURE 4A

```
PTPH1          NLDKNRYKDVLPYDTTRVLLQGN------------------------------EDYINASYVNM
PTPase 1B      NKNRNRYRDVSPFDHSRIKLHQED------------------------------NDYINASLIKM
T-Cell PTPase  NRNRNRYRDVSPYDHSRVKLQNAE------------------------------NDYINASLVDI
Human CD45 D1  NQNKNRYVDILPYDYNRVELSEINGDAG---------------------------SNYINASYIDG
Human CD45 D2  NKSKNRNSNVIPYDYNRVPLKHELEMSKESEHDSDESSDDDSEEPSKYINASFIMS PTPH1          EIPAANLVNKYIATQGPLPHTCAQFWQVVWDQKLSLIVMLTTLTERGRTKCHQYWP---
PTPase 1B      EEAQR-----SYILTQGPLPNTCGHFWEMVWEQKSRGVVMLNRVMEKGSLKCAQYWPQK
T-Cell PTPase  EEAQR-----SYILTQGPLPNTCCHFWLMVWQQKTKAVVMLNRIVEKESVKCAQYWP-T
Human CD45 D1  FKEPR-----KYIAAQGPRDETVDDFWRMIWEQKATVIVMVTRCEEGNRNKCAEYWP---
Human CD45 D2  YWKPE-----VMIAAQGPLKETIGDFWQMIFQRKVKVIVMLTELKHGDQEICAQYWG---

PTPH1          -DPPDVMNHGGFHIQCQSEDCTIAYVSREMLVTN-TQTGEEHTVTHLQYVAWPDHGIP
PTPase 1B      EEKEMIFEDTNLKLTLISEDIKSYYTVRQLELEN-LTTQETREILHFHYTTWPDFGVP
T-Cell PTPase  DDQEMLFKETGFSVKLLSEDVKSYYTVHLLQLEN-INSGETRTISHFHYTTWPDFGVP
Human CD45 D1  SMEEGTRAFGDVVVKINQHKRCPDYIIQKLNIVNKKEKATGREVTHIQFTSWPDHGVP
Human CD45 D2  ---EGKQTYGDIEVDLKDTDKSSTYTLRVFELRH-SKRKDSRTVYQYQYTNWSVEQLP PTPH1          DDSSDFLEFVNYVR---------------SLRVDSEPVLVHCSAGIGRTGVLVTMETAMCLT
PTPase 1B      ESPASFLNFLFKVR----------ESGSLSPEHGPVVVHCSAGIGRSGTFCLADTCLLLM
T-Cell PTPase  ESPASFLNFLFKVR----------ESGSLNPDHGPAVIHCSAGIGRSGTFSLVDTCLVLM
Human CD45 D1  EDPHLLLKLRRRVN----------AFSNFFSGPIVVHCSAGVGRTGTYIGIDAMLEGL
Human CD45 D2  AEPKELISMIQVVKQKLPQKNSSEGNKHHKSTPLLIHCRDGSQQTGIFCALLNLLESA PTPH1          ERNLP----IYPLDIVRKMRDQRAMMVQTSSQYKFVCEAILRVYEEGLVQMLDPS
PTPase 1B      DKRKDPSSVDIKKVLLEMRKFRMGLIQTADQLRFSYLAVIEGAKFIMGDSSVQD
T-Cell PTPase  EKGDD----INIKQVLLNMRKYRMGLIQTPDQLRFSYMAIIEGAKCIKGDSSIQK
Human CD45 D1  EAENK----VDVYGYVVKLRRQRCLMVQVEAQYILIHQALVEYNQRGETEVNLSE
Human CD45 D2  ETEEV----VDIFQVVKALRKARPGMVSTFEQYQFLYDVIASTYPAQNGQVKKNN
```

FIGURE 4B

ISOLATION OF A CDNA ENCODING A PROTEIN TYROSINE PHOSPHATASE WHICH LOCALIZES TO FOCAL ADHESIONS

RELATED APPLICATION

This is a continuation of application Ser. No. 07/663,579 filed on Mar. 1, 1991, now abandoned, which is a CIP of application Ser. No. 07/494,036 filed Mar. 14, 1990, now abandoned.

FUNDING

Work described herein was funded by Cold Spring Harbor Laboratory.

BACKGROUND

Focal adhesion plaques are specialized regions of the plasma membrane through which cells in culture adhere to the external substrate (Burridge, K. et al., *Ann. Rev. Cell. Biol.*, 4:487–525 (1988); Burridge, K. and K. Fath, *BioEssays*, 10:104–108 (1989)). On their internal face these structures anchor actin stress fibres, which are important in determining cell shape. Similar, but less well-characterized structures have been implicated in attachment between neighboring cells and adherence to extracellular matrix in vivo. Oncogenic transformation is frequently accompanied by a less-adherent, rounded morphology resulting from reorganization of the cytoskeleton (Ben Ze'ev, A., *Biochem. Biophys. Acta.*, 780:197–212 (1985; Felice, G. R. et al., *Eur. J. Cell Biol.*, 52:47–49 (1990)). In Rous Sarcoma Virus (RSV) transformed cells, for instance, it has been postulated that a contributing factor is the aberrant phosphorylation by $pp60^{v-src}$ of tyrosyl residues in key focal adhesion proteins (Burr, J. G. et al., *Proc. Natl. Acad. Sci. U.S.A.*, 77:3484–3488 (1980); Parsons, J. T. and M. J. Weber, *Curr. Topics in Microbiol. and Immunol.*, 147:79–127 (1989)). Phosphotyrosine has also been detected in focal adhesions (Maher, P. A. et al., *Proc. Natl. Acad. Sci. U.S.A.*, 82:6576–6580 (1985)) and apical junctions (Takata, K. and S. J. Singer, *J. Cell Biol.*, 106:1757–1764 (1988)) in non-transformed cells, raising the possibility that tyrosine phosphorylation at these sites may regulate normal cellular function. Such phosphorylation events must be tightly controlled and an understanding of the mechanism(s) involved would be very useful in furthering our understanding of control of normal and neoplastic cell growth.

SUMMARY OF THE INVENTION

The present invention relates to DNA which encodes a protein homologous to the protein tyrosine phosphatases (PTPases) which catalyze the dephosphorylation of proteins in which tyrosyl residues have been phosphorylated through the action of a protein kinase. The protein, which appears as if it will localize to focal adhesions, is also the subject of the present invention. In particular, it relates to cDNA encoding a protein, referred to as PTPH1, which was obtained from HeLa cells and characterized. PTPH1 has also been identified in other cell types. The structure of PTPH1 includes three segments: 1) an N-terminal segment of approximately 320 residues, which shows homology with the N-terminal segments of the talin family in the region known to be important for localization to focal adhesions; 2) a central segment, in which there are sequences with the features of sites of phosphorylation by casein kinase 2 and $p34^{cdc2}$, which may be important for regulation of phosphatase activity; and 3) a C-terminal segment of approximately 250 residues, which shows homology to the known members of the PTPase family. PTPH1 has a single putative catalytic domain.

Because of its homology with the talin family of proteins, which are known to participate in linkage of intracellular actin filaments to the extracellular matrix at focal adhesions, it is likely that PTPH1 localizes to the focal adhesions, which is a major site of action for oncogenic protein tyrosine kinases (PTK). Thus, overexpression of PTPH1 may be a powerful approach to countering the effects of oncogenic protein tyrosine kinases, such as those of transforming viruses, and interfering with or reversing cell transformation. This would provide a means of preventing or reversing abnormally high levels of phosphotyrosine associated with any disease or condition, such as preventing or reversing malignancy associated with the activity of a protein tyrosine kinase. Such protein tyrosine kinase may be of viral origin or be a cellular protein tyrosine kinase whose normal cellular function is disrupted, resulting in abnormal phosphorylation of tyrosyl residues. Such a method of preventing or reversing malignancy caused by or associated with the activity of a protein tyrosine kinase is also the subject of the present invention. In the present method, DNA or RNA encoding PTPH1 or a functional equivalent of PTPH1 is administered to an individual in an appropriate gene transfer vehicle which can infect mammalian cells and, once inside the mammalian cells, express and make available PTPH1 or its functional equivalent in sufficient quantities to overcome or counteract the protein tyrosine kinase activity. As a result, phosphorylation of tyrosine residues at abnormal levels is prevented or reversed, resulting in turn in prevention or reversal of malignancy of cells. Suitable gene transfer vehicles are those which contain DNA or RNA encoding PTPH1 or a PTPH1 functional equivalent, can infect mammalian cells and express the encoded protein within the infected mammalian cells. Such vehicles include recombinant retroviruses and recombinant vaccinia virus.

The method of the present invention is useful in treating or preventing a wide variety of conditions in which abnormally high levels of phosphotyrosine occur and particularly in treating or preventing malignancies in which tyrosyl phosphorylation by a protein tyrosine kinase occurs at an abnormal rate or level and in which dephosphorylation of tyrosyl residues by PTPH1 or its functional equivalent results in prevention or reversal of a malignant phenotype.

BRIEF DESCRIPTION OF THE DRAWINGS

FIGS. 1A–1B show the nucleotide sequence and the deduced amino acid sequence of PTPH1.

FIG. 4 shows the alignment of the amino acid residues of PTPH1 and the conserved domains in related proteins. FIG. 4A is a comparison of the sequence of the N-terminal segment PTPH1 with the homologous domain in band 4.1, ezrin and talin. FIG. 4B is a comparison of the PTPase-like domain in PTPH1 with the catalytic domains of two low Mr. PTPases (PTP1B and TCPTP) and a receptor linked form (CD45).

DETAILED DESCRIPTION OF THE INVENTION

Figure 2:
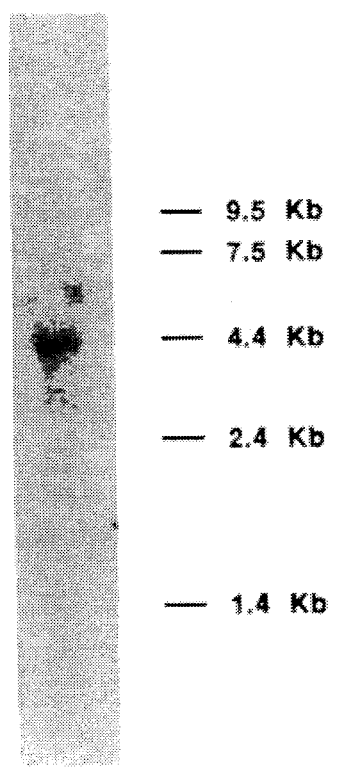
FIG. 2 shows the results of northern blot analysis of PTPH1 mRNA from HeLa cells.

The present invention relates to DNA encoding a protein tyrosine phosphatase which appears to localize to focal adhesions. In particular, it relates to PTPH1, which in one segment is homologous to the protein tyrosine phosphatases (PTPases) and in another segment is homologous to a family of proteins which are located at the interface between the plasma membrane and the cytoskeleton. The present invention also relates to the encoded PTPH1 protein, RNA encoding the PTPH1 protein, antibodies specific for PTPH1 protein and methods of using the DNA encoding PTPH1 and the PTPH1 protein. DNA encoding PTPH1 can be used to prevent or reverse phosphorylation of tyrosine residues in proteins which have been phosphorylated by a protein tyrosine kinase.

As described herein, a protein which is a homologue of the protein tyrosine phosphatases has been identified by means of amplification of PTPase-related cDNAs. In addition, the deduced amino acid sequence of PTPH1 has been compared with the amino acid sequences of other proteins with known activities. As a result, PTPH1 has been shown to have three segments. As described below, the characteristics of at least two of these regions make it reasonable to expect that PTPH1 localizes to the focal adhesions and has intrinsic phosphatase activity.

The following is a summary of aspects of cytoskeletal components and maintenance of cytoskeletal integrity and description of the identification of PTPH1. Also described are the possible role of PTPH1 in maintaining cytoskeletal integrity and preventing or reversing tyrosyl phosphorylation and a method of preventing or reversing malignant transformation of mammalian cells. In the method of preventing or reversing malignant transformation, DNA or RNA encoding PTPH1 or a PTPH1 functional equivalent is introduced into cells and expressed in sufficient quantities to prevent or reverse abnormal tyrosyl phosphorylation, resulting in prevention of transformation of the cells or reversal of the malignant phenotype.

The actin stress fibres are a component of the cytoskeleton that are important for the determination of cell shape and also for attachment to the substratum. These actin cables interact with the cell membrane at regions described as focal contacts, focal adhesions or adhesion plaques. Fibronectin is an extracellular glycoprotein that is arranged in immobilized fibrillar arrays across the surface of many cells, forming network that interconnects cells with each other. The receptors for fibronectin on the cell surface are termed integrins. Integrins are also localized to focal adhesions and provide the transmembrane link between components of the extracellular matrix, such as fibronectin and vitronectin, and the cytoskeleton.

Progress has been made in identifying the components of the focal adhesions that provide the link between the integrins and the actin fibres; however, the picture is not yet complete. At present it is thought that the integrins interact indirectly with actin cables through a multiprotein complex. Talin interacts with the cytoplasmic segment of the integrin β chain and also binds to vinculin. Vinculin has been shown to interact with α actinin, which can bind actin directly. Of these components, vinculin, talin and the β subunit of the integrins are phosphorylated on tyrosyl residues. A correlation has yet to be established between such phosphorylation and the appearance of the transformed phenotype. However, this picture is undoubtedly imcomplete. Other substrates of tyrosine phosphorylation, including two focal adhesion associated proteins, paxillin and ezrin, have also been identified. Furthermore, microtubules and intermediate filaments may also terminate at focal adhesions but the nature of the proteins that facilitate this interaction is unknown. Thus, additional focal adhesion associated proteins remain to be characterized and their function established. Protein and cDNA sequence analysis has defined a family of proteins that include talin (Rees, D. J. G. et al., *Nature*, 347:685–689 (1990)), ezrin (Turunen, O. et al., *J. Biol. Chem.*, 264:16727–16732 (1989); Gould, K. L. et al., *EMBO J.*, 8:4133–4142 (1989)) and band 4.1, (Conboy, J. et al., *Proc. Natl. Acad. Sci. U.S.A.*, 83:9512–9516 (1986)) which participate in the interaction between the membrane and cytoskeleton. They possess a homologous N-terminal domain that appears to associate with protein components in the plasma membrane. In band 4.1, which promotes association of actin and spectrin in erythrocytes, this domain interacts with the transmembrane protein glycophorin (Bennett, V., *Biochem. Biophys. Acta.*, 988:107–121 (1989)). A similar model has been proposed for the interaction of talin with integrin (Rees, D. J. G. et al., *Nature*, 347:685–689 (1990)). In the case of ezrin, which displays a submembranous localization in brush border cells, the details of its interaction with other proteins remain to be established.

Identification of the complement of protein tyrosine phosphatases in HeLa cells was carried out as described in detail in Example 1. Briefly, protein tyrosine phosphatase-related cDNAs were amplified in the polymerase chain reaction (PCR) using primers corresponding to conserved segments within the catalytic domains. The PCR reaction products (approximately 0.25 kb) were subcloned into pUC118; of 77 independent subclones sequenced, 15 corresponded to a novel PTPase isoform termed PTPH1. A total of $4.2 \times 10^6$ phage plaques from the same HeLa cell cDNA library were probed with the PCR product and 10 positive clones were identified.

Figure 1A:
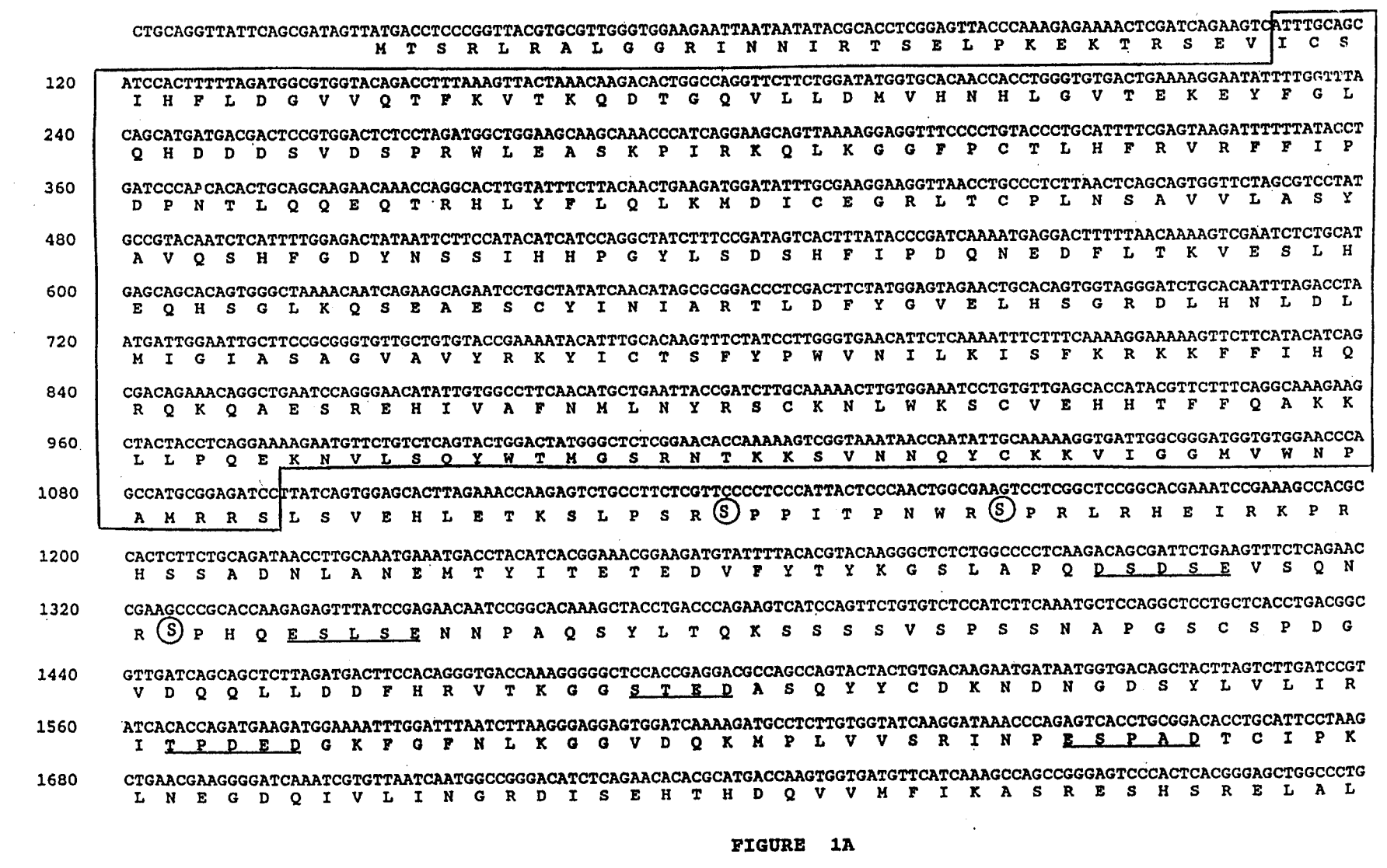
Figure 1B:
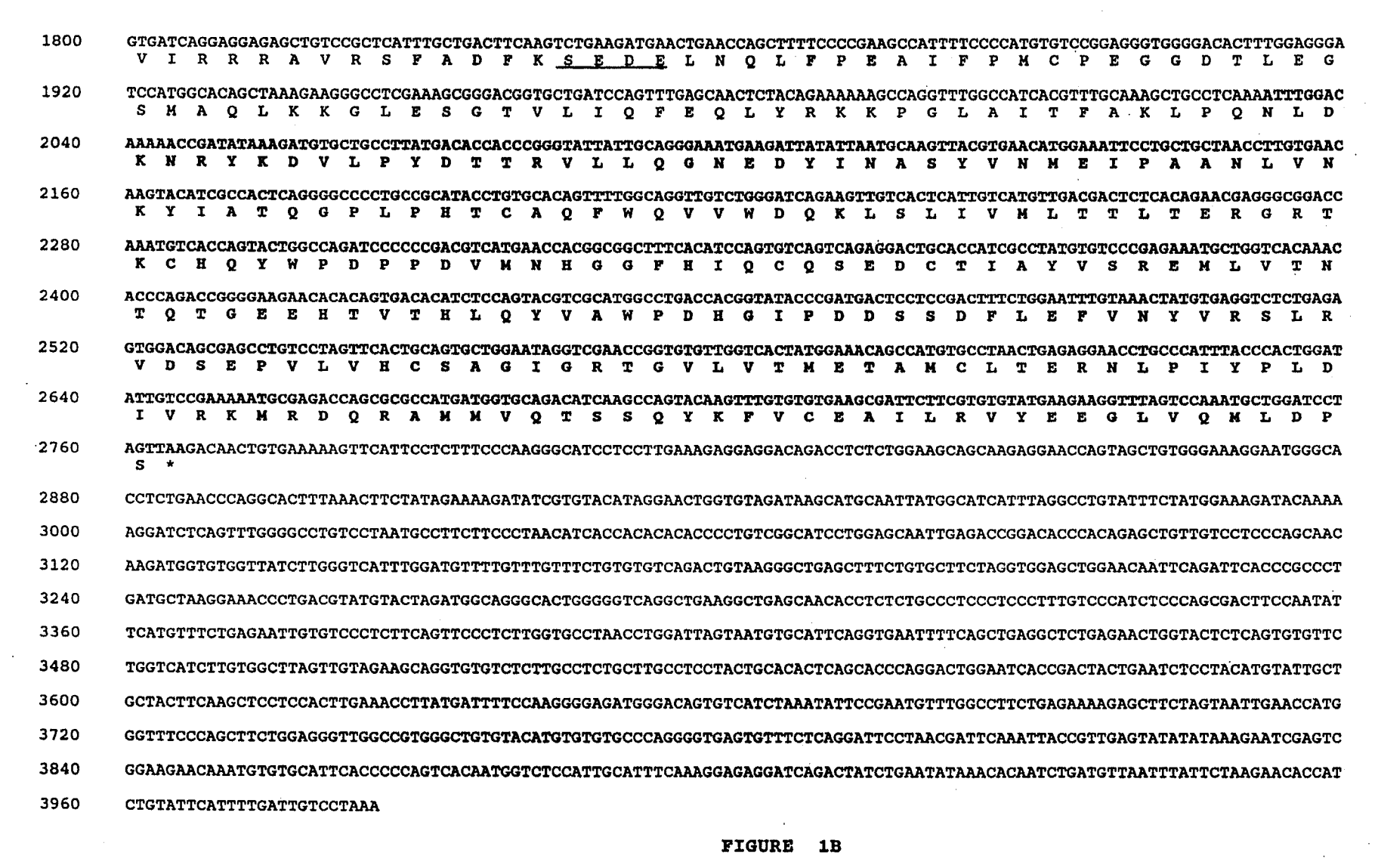

The sequence of the longest clone (3984 bp) is presented in FIGS. 1A–1B. It has a 5'-noncoding segment of 23 bp followed by an open reading frame, from the first available ATG, of 2739 bp. This open reading frame would encode a protein of 913 amino acids with a predicted Mr of approximately 104k. Although the sequence surrounding the putative initiator does not conform well to the Kozak consensus sequence (Kozak, M., *J. Cell. Biol.*, 108:229–241 (1989)), there is a purine at position -3 which is an important requirement for an initiation site. Furthermore, translation of RNA, synthesized from PTPH1 cDNA, in a reticulocyte lysate yielded a protein of approximately 120 kDa, close to the expected size. There is a 3' non-translated segment of 1222 bp, but the cDNA does not contain a consensus polyadenylation signal or a poly A tail. A transcript encoding PTPH1 was detected by northern blot analysis of HeLa cell polyA+ mRNA as a low abundance message of approximately 4.3 kb (FIG. 2). The slightly larger size of the mRNA may be explained in part by the absence of a poly A tail in the cDNA.

Figure 3:
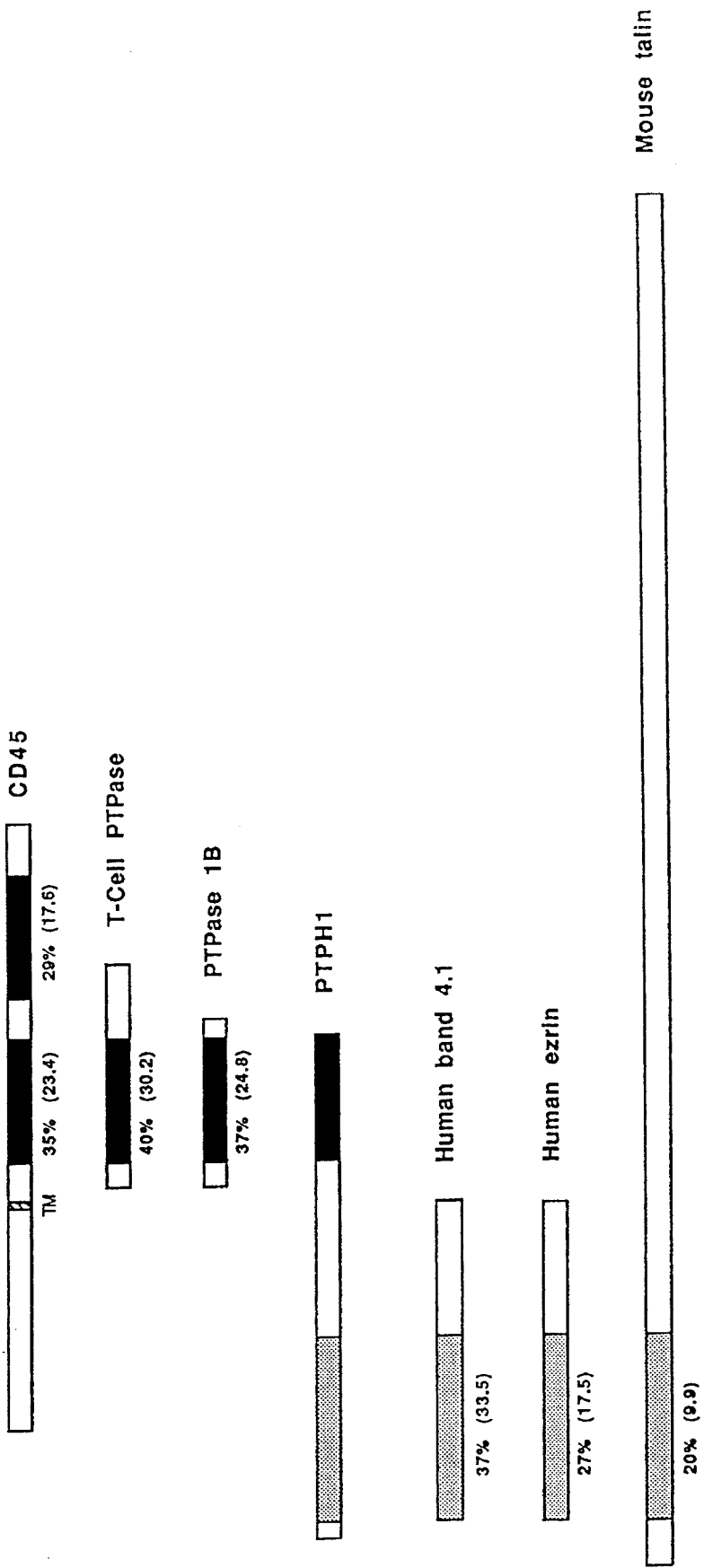
FIG. 3 is a schematic diagram illustrating the structure of PTPH1 and its relationship to CD45, T-cell PTPase and PTPase 1B and human band 4.1, human ezrin and mouse talin.

The sequence of PTPH1 can be described in terms of 3 segments, as summarized in FIG. 3. The alignment of amino acid residues of PTPH1 and the conserved domains in related proteins was also assessed. The results are represented in FIG. 4. In FIG. 4A, the sequence of the N-terminal segment of PTPH1 is compared with the homologous domain in 4.1, ezrin and talin. As shown in FIG. 4A, the N-terminal segment of PTPH1 is homologous to the domains in band 4.1, ezrin and talin that have been proposed to function in localizing these proteins to the interface between the plasma membrane and the cytoskeleton (Rees, D. J. G. et al., *Nature*, 347:685–689 (1990)).

In FIG. 4B, the sequence of the protein tyrosine phosphatase-related domain of PTPH1 is compared with the catalytic domains of two low Mr PTPases (PTP1B and TCPTP) and a receptor-linked form (CD45). The C-terminal segment displays homology to the catalytic domain of the PTPases (FIG. 4B). As shown in FIG. 1, the central segment contains sequences that suggest potential phosphorylation sites for casein kinase II and p34$^{cdc2}$. While the dephosphorylation of tyrosyl residues in proteins by PTPH1 remains to be demonstrated, it should be noted that in CD45 (Tonks, N. K., et al., *Biochemistry*, 27:8695–8701 (1988))) and LAR (Sreuli, M. et al., *EMBO J.*, 9:2399–2407 (1990)), which share comparable levels of sequence identity to PTP1B as displayed by PTPH1, intrinsic activity has been confirmed.

The PTPases comprise a rapidly expanding family of enzymes and it is anticipated that the various isoforms will have specific functions in vivo. The structure of PTPH1 may illustrate a general theme among the PTPases; within the protein, distinct structural motifs may, at least in part, control specificity by restricting intracellular localization. It is proposed that PTPH1 acts at the junction between the cytoskeleton and the plasma membrane and plays: a role in controlling cytoskeletal integrity. The occurrence of a signal peptide sequence and a transmembrane domain in CD45 directs it to span the membrane. The C-terminal, non-catalytic segment of the low Mr, cytoplasmic PTPases also appears to direct association with the particulate fraction of cell extracts. In addition such structural motifs may determine how the activity of the catalytic domain is controlled. Thus for the receptor-like forms the binding of ligands to the extracellular segments may modulate activity. The C-terminal segment of the low Mr PTPase appears to repress the activity of the catalytic domain. If PTPH1 is localized to focal adhesions it should also be regulated to permit normal tyrosine phosphorylation at such sites in non-transformed cells. Phosphorylation of Ser/Thr residues in the central segment of the protein (FIG. 1) may directly modulate activity. In addition, by analogy with band 4.1 whose affinity for glycophorin is regulated by phosphatidylinositol-4,5-bisphosphate, it is possible that the localization of PTPH1 may alter with phosphatidylinositol turnover.

Considering the apparent correlation between RSV induced transformation and the cytoskeletal association of pp60$^{src}$ (Burr, J. G. et al., *Proc. Natl. acad. Sci. U.S.A.*, 77:3484–3488 (1980); Shriver, K. and L. R. Rohrschneider, *Cold Spring Harbor Conference Cell Proliferation*, 8:*Protein Phosphorylation*, 1247–1262 (1981); Hamaguchi, M. and Hanafusa, H., *Proc. Natl. Acad. Sci. U.S.A.*, 4:2312–2316 (1987); Tapley, P. et al., *Oncogene*, 4:325–333 (1989); Glenney, J. R., Jr. and Zokas, L., *J. Cell Biol.*, 108:2401–2408 (1989) PTPH1 is an excellent candidate PTPase with which to achieve a reversion of src-induced transformation and furthermore to delineate the precise role of tyrosine phosphorylation in the morphological changes induced by src. In addition, it clearly has potential to function as growth suppressor; the inactivation or deletion of the PTPH1 could conceivably in itself be sufficient to generate a transformed phenotype.

It has been known for some time that viral transformation, for instance by Rous Sarcoma Virus (RSV), brings about a decrease in cell adhesion that is associated with a rounding up of the cells, a reduction in the number of stress fibres and a loss of fibronectin-integrin association. In RSV transformed cells the number of focal adhesions is dramatically decreased and those that remain are altered in architecture. The transforming protein tyrosine kinase of RSV, pp60$^{v\text{-}src}$, is localized to the adhesion plaques; this is associated with an increased level of phosphotyrosine in these structures. In fact, the level of phosphotyrosine in the focal adhesions correlates with the density of actin stress fibres. That is, the higher the level of phosphotyrosine, the less intact is the cytoskeleton. Therefore, it appears that the association of pp60$^{v\text{-}src}$ with the focal adhesions and the phosphorylation of tyrosyl residues in proteins within this structure are intimately involved in the disruption of the cytoskeleton.

Transforming genes, oncogenes, are mutated forms of normal cellular genes, termed proto-oncogenes. Malignant transformation can be described as a disruption of the normal modes of growth control, that is, transformed cells can divide in the absence of specific growth stimulatory factors or fail to respond to growth inhibitory signals. In other words, transformation may often result from the disruption of a normal cellular process. In this regard, it is interesting to note that in the normal process of mitosis, the cells round up and there is a transient disruption of focal contacts.

Antibodies to phosphotyrosine have indicated that tyrosine phosphorylation of focal adhesion (Maher, P. A. et al., *Proc. Natl. Acad. Sci. U.S.A.*, 82:6576–6580 (1985)) and apical junction (Takata, K. and S. J. Singer, *J. Cell Biol.*, 106:1757–1764 (1988)) proteins also occurs in non-transformed cells, suggesting the action of a PTK at these sites in normal cell function. However, the kinases involved have yet to be identified. In view of the potentially disastrous effects of aberrant tyrosine phosphorylation one would anticipate that the action of such PTKs would be tightly controlled. The localization of a PTPase to these structures is one means by which such regulation could be achieved.

The protein tyrosine phosphatases have been shown to constitute a family of both cytoplasmic, low-Mr and transmembrane receptor-linked forms. The work described herein has resulted in identification of a novel homologue of the protein tyrosine phosphatases in epithelial cells, specifically HeLa cells, which are a model system for the study of the cell cycle. As described, this protein tyrosine phosphatase (PTPH1) has homology with the talin family of proteins and, therefore, can be expected to localize to the interface between the plasma membrane and the cytoskeleton, such as at focal adhesions, which are a major site of action of oncogenic protein tyrosine kinases. Such a protein tyrosine phosphatase is referred to herein as one which localizes to the interface between the plasma membrane and the cytoskeleton. Overexpression of PTPH1 can be used to counter the effects of protein tyrosine kinases, such as v-src.

As a result of the findings described herein, a protein tyrosine phosphatase which appears to localize to focal adhesions, which is a major site of action for oncogenic protein tyrosine kinases is available, as are DNA and RNA encoding the protein. The ability of PTPH1 or a functional equivalent to reverse malignant transformation of cells can be assessed using known methods. For example, this can be carried out as follows: briefly, cells, for instance chicken embryo fibroblasts or NIH 3T3 cells, which are transformed by introduction of a viral oncogene such as v-src, display a change in morphology relative to the non-transformed controls. They will grow in soft agar and induce tumor formation in nude mice. Trnasformed cells are transfected with the PTPH1 DNA using an appropriate expression vector. The ability of PTPH1 DNA or its functional equivalent to have the desired effect is assessed by determining whether the transformed phenotype is maintained or reversed after PTPH1 DNA or its functional equivalent is introduced into the transformed cells. Reversal of the phenotype is indicative of the ability of the introduced DNA to counter the effects of the kinase. These effects can also be examined at the level of changes in the phosphorylation state of tyrosyl residues in intracellular proteins.

Transformed cells are transfected with the PTPH1 DNA using an appropriate expression vector. The ability of PTPH1 DNA or its functional equivalent to have the desired effect is assessed by determining whether the transformed phenotype is maintained or reversed. Reversal of the phenotype is indicative of the ability of the introduced DNA to counter the effects of the kinase.

Thus, an agent and a method for preventing or reversing the malignant transformation of cells associated with or caused by the activity of a protein tyrosine kinase are now available. The agent can be DNA or RNA encoding PTPH1 or its functional equivalent. A functional equivalent of PTPH1 has substantially the same sequence as that shown in FIGS. 1A–1B, and can catalyze dephosphorylation of tyrosyl residues phosphorylated through the action of a protein tyrosine kinase. As used herein, the term PTPH1 includes the protein whose amino acid sequence is represented in FIGS. 1A–1B and its functional equivalents, as defined above. Modified or mutated PTPH1-encoding DNA (i.e., DNA which differs from the PTPH1 DNA of FIGS. 1A–1B by at least one addition, deletion or substitution) can also be used.

In the method of the present invention, DNA encoding PTPH1 or its functional equivalent is introduced into an individual in whom its effects are desired. It is introduced in a recombinant vehicle, such as, but not limited to, retrovirus or vaccinia virus. All or a portion of the PTPH1 DNA or RNA can be used, provided that it is sufficient to express in host cells a protein or peptide with the PTPase activity. PTPH1-encoding DNA can be introduced into a retroviral vector, such as those described in the literature, using known methods (See, for example, Yu et al., *Proc. Natl. Acad. Sci U.S.A.*, 83:3194–3198 (1986); Markowitz et al., *J. Virol.*, 62:1120–1124 (1988); Cepko et al., *Cell*, 37:1053–1062 (1984); Mann et al., *Cell*, 33:153–159 (1983); Cone et al., *Proc. Natl. Acad. Sci. U.S.A.*, 81:6349–6353 (1984)). Alternatively, it can be introduced into vaccinia virus, using known methods.

The resulting recombinant gene transfer vehicle, which contains all or a portion of the PTPH1 DNA (or RNA), is introduced into an individual in sufficient quantities to prevent malignant transformation associated with phosphorylation of tyrosyl residues in proteins via a protein tyrosine kinase-catalyzed reaction. The PTPH1 DNA-containing vehicle can be introduced by a variety of routes (e.g., intraperitoneally, intramuscularly, intravascularly) and will generally be introduced in combination with a carrier (e.g., physiological saline or suitable buffer).. This method is useful in the treatment or prevention of a variety of malignancies, including breast cancer and leukemia.

Exemplification Identification of PTPH1

Oligonucleotide primers were synthesized based on the conserved sequences KCAQYWP (#1, equivalent to residues 120–126 in PTP1B) and HCSAGIG (#2, equivalent to residues 214–220 in PTP1B). The degeneracy of the first primer was 64 fold and that of the second 96 fold. Phage DNA of a HeLa cell cDNA library (Stratagene) isolated by the plate lysate method (Sambrook, J. et al., *Molecular Cloning: A Lab Manual*, 2d (1989)) was used as template. Primers were phosphorylated with T4 polynucleotide kinase (New England Biolabs) prior to PCR and were added at a final concentration of 1 µM to a mixture containing 10 mM Tris-HCl (pH8.4), 50 mM KCl, 1.5 mM $MgCl_2$, 0.01% gelatin, 20 mM dNTPS, 2.5 units of Taq polymerase (Perkin-Elmer/Cetus) and 2 µg phage DNA. Thirty cycles of the PCR reaction were performed; each was carried out at 94° C. for 1 min, 50° C. for 1 min and 72° C. for 2 min. The PCR products were analyzed on a 1% agarose gel and DNA fragments of approximately 0.25 kb were excised, eluted from the gel, subcloned into the SmaI site of pUC118 and sequenced. The same HeLa cDNA library was probed with the 0.25 kb PTPH1 product of PCR obtained above. Plaques were transferred to nitrocellulose filters (Schleicher & Schuell) and screened by hybridization at 65° C. in a solution containing 2×SSC (SSC=0.15M NaCl, 0.015M trisodium citrate), 5×Denhardt's, 0.1% SDS, 25 mM sodium phosphate, 1% sodium pyrophosphate, 10% dextran sulfate and 12.5 µg/ml denatured calf thymus DNA. The filters were washed successively at the same temperature in a series of solutions containing 0.1% SDS with 4× SSC, 2× SSC, 1× SSC and finally 0.1× SSC. Hybridizing phage were plaque purified, DNA was prepared and cDNA inserts were isolated and subcloned using standard techniques (Sambrook, J. et al., *Molecular Cloning: A Lab Manual*, 2d (1989)). DNA sequencing was carried out by the dideoxynucleotide chain-termination procedure (Sanger, F. et al., *Proc. Natl. Acad. Sci. U.S.A.*, 74:5463–5467 (1977)) using either manufacturer's primers (United States Biochemical Corporation) or synthetic oligonucleotides derived from the existing sequences. The GenBank database of sequence information was searched with the FASTA program of Pearson and Lipman to identify proteins with amino acid sequence similar to that of PTPH1.

The nucleotide sequence of the cDNA designated PTPH1 and the predicted amino acid sequence are represented in FIGS. 1A–1B. The open box delineates the segment of homology to the N-terminal domain of band 4.1, ezrin and talin. The bold region defines the segment homologous to the catalytic domains of the PTPases. In the intervening segment, seryl and threonyl residues located in sequences bearing features of sites of casein kinass II phosphorylation sites are underlined. The primary structure requirements for casein kinass II phosphorylation include the presence of surrounding acidic residues. An Asp or Glu three residues to the C-terminus of the phosphate acceptor site is particularly critical (Kuenzel, E. A. et al., *J. Biol. Chem.*, 262:9136–9140 (1987)). The presence of prolyl residues preceeding the phosphorylation site is also common. In addition, seryl residues 372 and 381 display some features of potential sites of phosphorylation by $p34^{cdc2}$ (Moreno, S. and P. Nurse, *Cell* 61:549–551 (1990)).

Northern analysis of PTPH1 mRNA was also carried out. Total RNA was extracted from HeLa cells and Poly(A)+ RNA was selected by oligo(dT)cellulose chromatography as described by Sambrook, J. et al. (Sambrook, J. et al., *Molecular Cloning: A Lab Manual*, 2d (1989)). After electrophoresis on a formaldehyde-agarose (1%) gel, the RNA was transferred to a Gens Screen Plus membrane and hybridized with the 4kb insert of PTPH1. The hybridization and washing conditions were the same as described above, except that SDS was included at 1%. Results are shown in FIG. 2. Numbers on the right indicate the size of RNA markers (BRL).

The relationship of the structure of PTPH1 was assessed and compared with that of other proteins. This assessment showed that PTPH1 comprises three segments, as represented in FIG. 3: an N-terminal segment (shaded) with homology to the membrane localization domains in band 4.1, ezrin and talin, a putative regulatory segment in the middle of the protein (open) and a C-terminal PTPase related segment (black). TM denotes the transmembrane domain in CD45. The length of each protein is shown in proportion to its molecular weight. The homology among domains is indicated by their percentage identity expressed as the number of identities out of possible matches between residues in the aligned sequences. In addition the numbers in parentheses are alignment scores, which express the similarity of segments in units of standard deviation from the average background scores of 100 randomly generated sequences. The alignments were optimised using the ALIGN programme from the National Biomedical Research Foundation, the mutation data matrix and a gap penalty of 10. Scores of >5 suggest homologyo Residues 3–357 in PTPH1 were compared pairwise with 2–323 in band 4.1, 4–339 in ezrin and 120–455 in talin. Residues 669–913 in PTPH1 were compared pairwise with 40–289 in PTP1B, 42–273 in TCPTPase, 491–738 in CD45 domain I and 782–1054 in CD45 domain II.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. Isolated DNA encoding the protein tyrosine phosphatase whose amino acid sequence is shown in FIGS. 1A–1B.

2. Isolated DNA comprising the nucleic acid sequence shown in FIGS. 1A–1B.

3. Isolated DNA of claim 1 wherein the isolated DNA is isolated from a human carcinoma.

4. Isolated DNA of claim 1 wherein the DNA is isolated from a HeLa cell library.

5. Isolated DNA of claim 2, wherein the DNA is isolated from a HeLa cell library.

6. A retroviral vector comprising DNA encoding the protein tyrosine phosphatase whose amino acid sequence is shown in FIGS. 1A–1B.

7. A retroviral vector comprising the nucleotide sequence shown in FIGS. 1A–1B.

* * * * *